United States Patent [19]

Clark et al.

[11] Patent Number: 5,713,853
[45] Date of Patent: Feb. 3, 1998

[54] METHODS FOR TREATING THROMBOSIS

[75] Inventors: David W. Clark; Souise S. Clark, both of Eden Prairie; Michael R. Forman, St. Paul, all of Minn.

[73] Assignee: Interventional Innovations Corporation, Minneapolis, Minn.

[21] Appl. No.: 488,216

[22] Filed: Jun. 7, 1995

[51] Int. Cl.$^6$ .............................................. A61M 31/00
[52] U.S. Cl. .............................. 604/53; 604/49; 604/104; 604/264; 606/200
[58] Field of Search .................... 604/19, 27–8, 604/48–9, 52–3, 93, 96, 104–7, 158, 161, 174–5, 264, 280; 606/191, 194, 198, 200

[56] References Cited

U.S. PATENT DOCUMENTS

| | | | |
|---|---|---|---|
| 3,472,230 | 10/1969 | Fogarty . | |
| 3,952,747 | 4/1976 | Kimmell, Jr. . | |
| 4,430,083 | 2/1984 | Ganz et al. | 604/283 |
| 4,488,877 | 12/1984 | Klein et al. | 604/175 |
| 4,494,531 | 1/1985 | Gianturco . | |
| 4,636,195 | 1/1987 | Wolinsky | 604/53 |
| 4,643,184 | 2/1987 | Mobin-Uddin . | |
| 4,693,243 | 9/1987 | Buras | 128/207.15 |
| 4,706,671 | 11/1987 | Weinrib . | |
| 4,737,141 | 4/1988 | Spits | 604/28 |
| 4,790,812 | 12/1988 | Hawkins, Jr. et al. | 604/27 |
| 4,793,348 | 12/1988 | Palmaz . | |
| 4,813,925 | 3/1989 | Anderson, Jr. et al. | 604/8 |
| 4,824,436 | 4/1989 | Wolinsky | 604/53 |
| 4,873,978 | 10/1989 | Ginsburg | 606/200 |
| 4,874,360 | 10/1989 | Goldberg et al. | 604/8 |
| 4,878,893 | 11/1989 | Chin | 604/105 |
| 4,887,996 | 12/1989 | Bengmark | 604/54 |
| 4,950,258 | 8/1990 | Kawai et al. | 604/281 |
| 4,957,470 | 9/1990 | Roemer | 604/8 |
| 4,986,814 | 1/1991 | Burney et al. | 604/164 |
| 4,994,069 | 2/1991 | Ritchart et al. | 606/191 |
| 4,997,435 | 3/1991 | Demeter | 606/127 |
| 5,034,001 | 7/1991 | Garrison et al. | 604/53 |
| 5,035,706 | 7/1991 | Gianturco et al. | 606/198 |
| 5,062,829 | 11/1991 | Pryor et al. | 604/57 |
| 5,087,244 | 2/1992 | Wolinsky et al. | 604/53 |
| 5,133,733 | 7/1992 | Rasmussen et al. | 606/200 |

(List continued on next page.)

OTHER PUBLICATIONS

Robert M. Califf, M.D., "Use of a Monoclonal Antibody Directed Against the Platelet Glycoprotein IIb/IIIa Receptor in High-Risk Coronary Angioplasty," *The New England Journal of Medicine*, Apr. 7, 1994, pp. 956–960.

Peter Eichelter, M.D. and Worthington G. Schenk, Jr., M.D., "A New Experimental Approach to Prophylaxis of Pulmonary Embolism," *Forefront: Preliminary Report*, Nov.–Dec. 1967, pp. 455–456.

(List continued on next page.)

*Primary Examiner*—Michael Powell Buiz
*Assistant Examiner*—Bhisma Mehta
*Attorney, Agent, or Firm*—Merchant, Gould, Smith, Edell, Welter & Schmidt, P.A.

[57] ABSTRACT

A catheter for delivering drugs or other agents is disclosed particularly suited for delivering drugs proximate the walls of a vessel or lumen, such as an artery or vein. The catheter comprises a shaft with a distal portion comprising at least one and preferably a plurality of delivery members. When deployed, the delivery members flare from the catheter shaft at an acute or obtuse angle. At least a portion of the delivery members are within a restraining member such as a sleeve or thread, for example, to maintain the delivery member within the diameter of the shaft prior to deployment. Delivery lumens provide drugs to ports in the delivery members for delivery out of the catheter. The delivery members preferably bear against the wall of the vessel when deployed, to deliver the drug or other agent proximate the walls of the blood vessel, where blood flow is slow. In another embodiment the delivery members comprise a first tapered portion, a second longitudinal portion and a plurality of drug delivery ports.

7 Claims, 12 Drawing Sheets

U.S. PATENT DOCUMENTS

| | | | |
|---|---|---|---|
| 5,147,379 | 9/1992 | Sabbaghian et al. | 606/206 |
| 5,152,777 | 10/1992 | Goldberg et al. | 606/200 |
| 5,160,342 | 11/1992 | Reger et al. | 606/200 |
| 5,181,911 | 1/1993 | Shturman | 604/96 |
| 5,221,261 | 6/1993 | Termin et al. | 604/104 |
| 5,242,452 | 9/1993 | Inoue | 606/198 |
| 5,256,146 | 10/1993 | Ensminger et al. | 604/104 |
| 5,267,960 | 12/1993 | Hayman et al. | 604/106 |
| 5,279,565 | 1/1994 | Klein et al. | 604/105 |
| 5,304,120 | 4/1994 | Crandell et al. | 604/52 |
| 5,324,304 | 6/1994 | Rasmussen | 606/200 |
| 5,336,178 | 8/1994 | Kaplan et al. | 604/53 |
| 5,342,348 | 8/1994 | Kaplan | 604/891.1 |
| 5,350,398 | 9/1994 | Pavcnik et al. | 606/200 |
| 5,370,657 | 12/1994 | Irie | 606/200 |
| 5,383,887 | 1/1995 | Nadal | 606/200 |
| 5,413,586 | 5/1995 | Dibie et al. | 606/200 |
| 5,415,630 | 5/1995 | Gory et al. | 604/53 |
| 5,509,900 | 4/1996 | Kirkman | 604/104 |
| 5,527,280 | 6/1996 | Goelz | 604/104 |

OTHER PUBLICATIONS

Peter Eichelter and Worthington G. Schenk, Jr., M.D., "Prophylaxis of Pulmonary Embolism, A New Experimental Approach With Initial Results," *Arch Surg—vol. 97*, Aug. 1968, pp. 348–356.

"Prolyser for Safe Temporary Protection," *Cordis International SA*, Jan. 1995, 3 pages.

"You Can See the Dispatch Difference," *1994 SCIMED Life Systems, Inc.*, 4 pages.

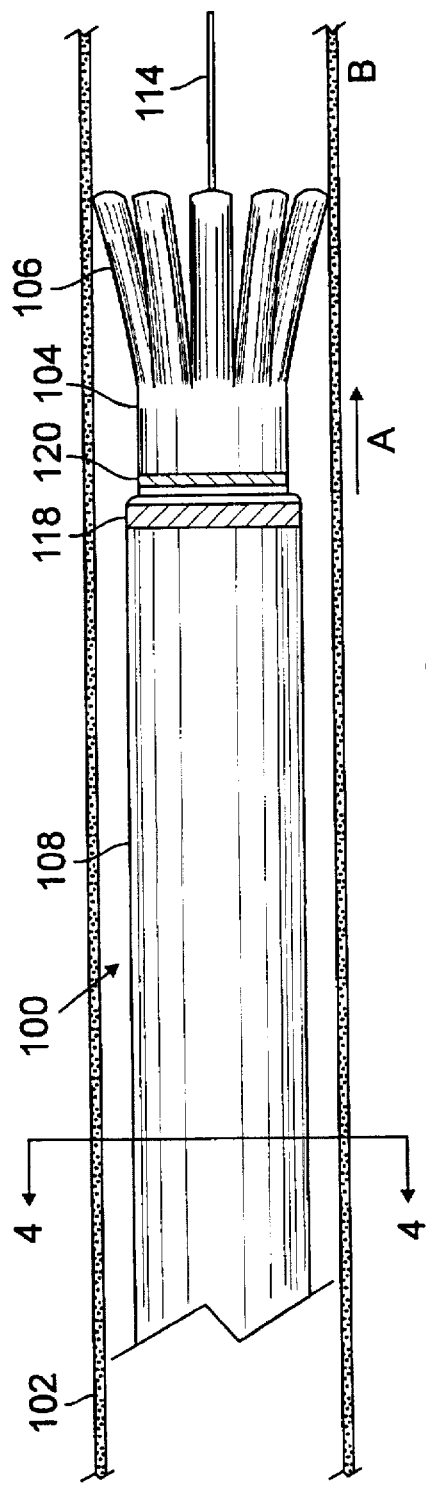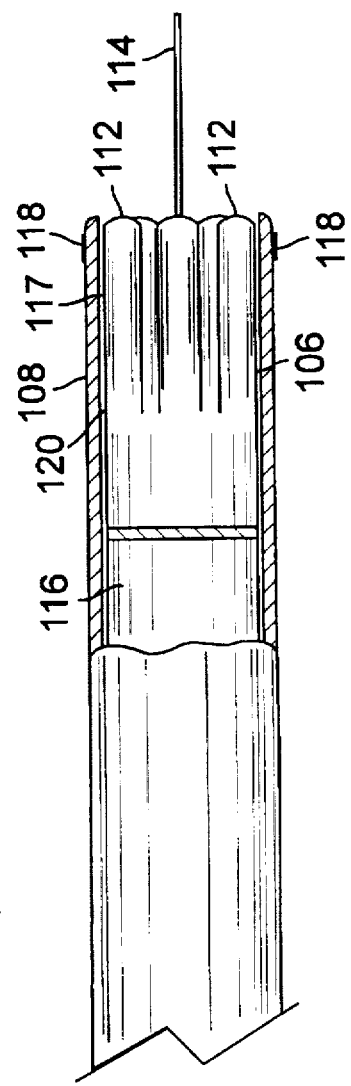
FIG. 1
FIG. 2

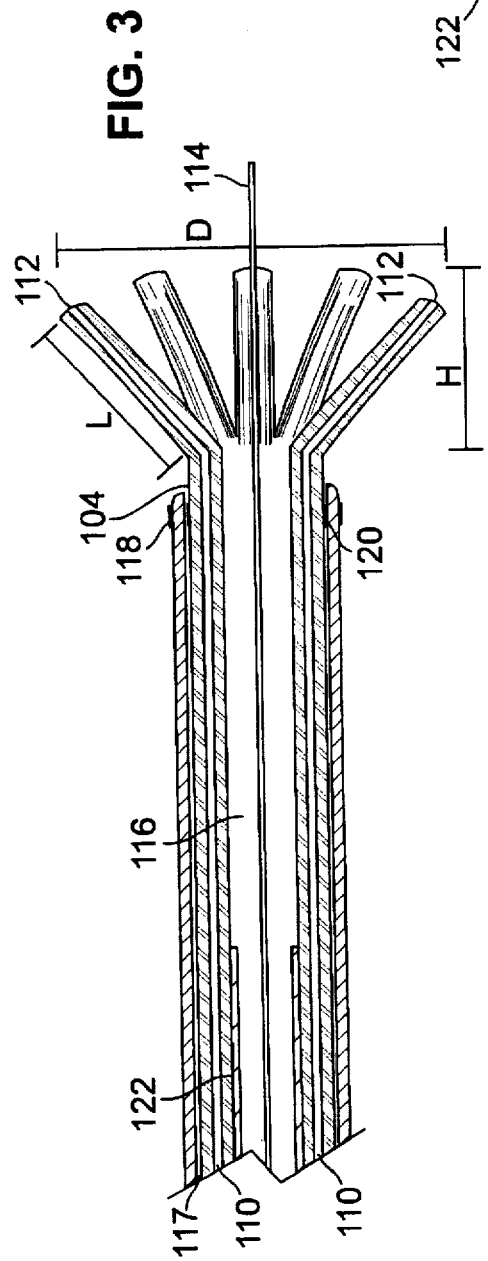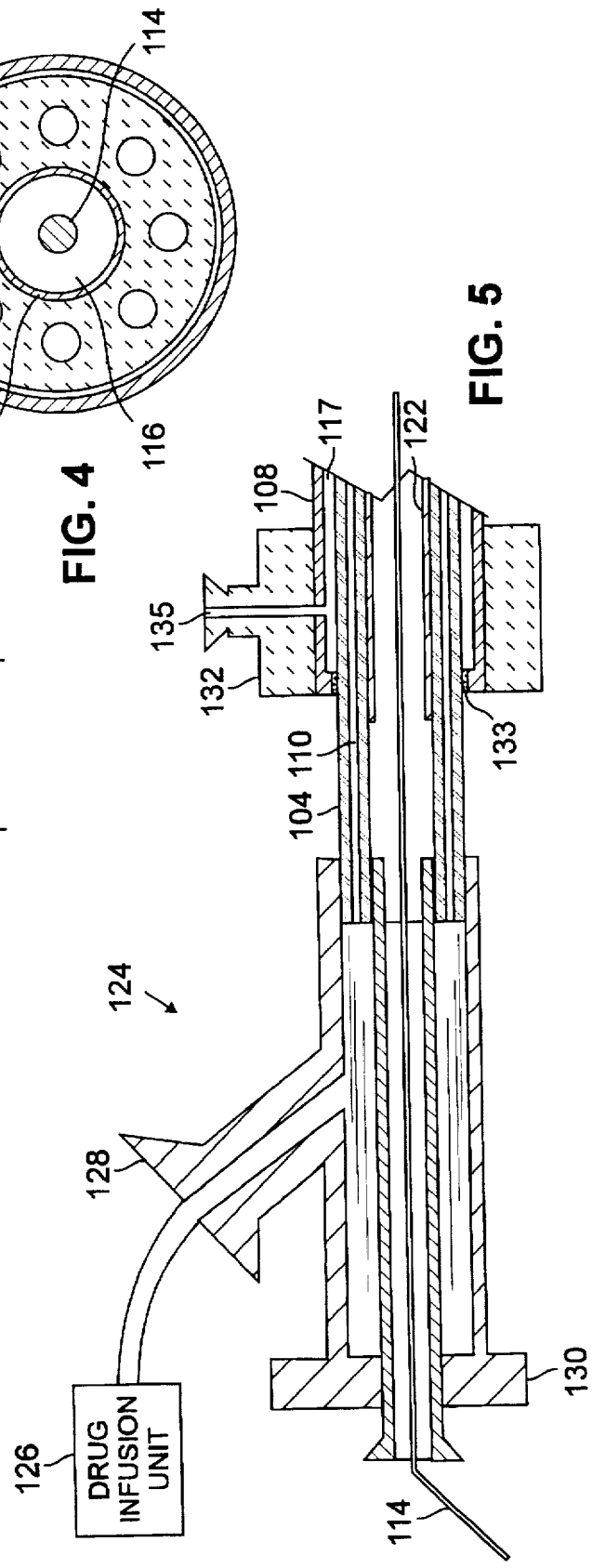

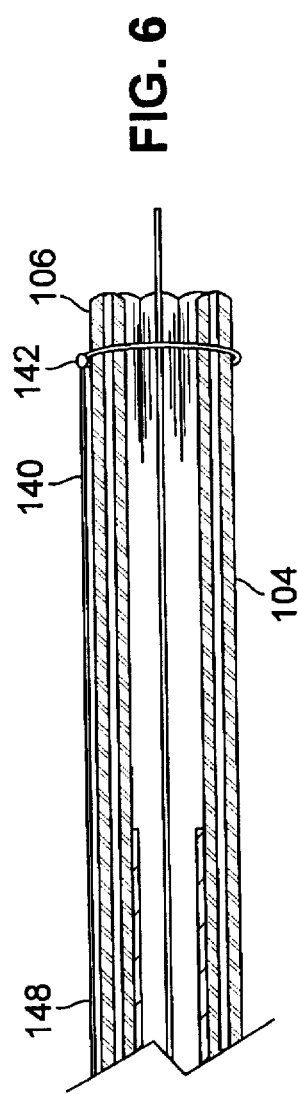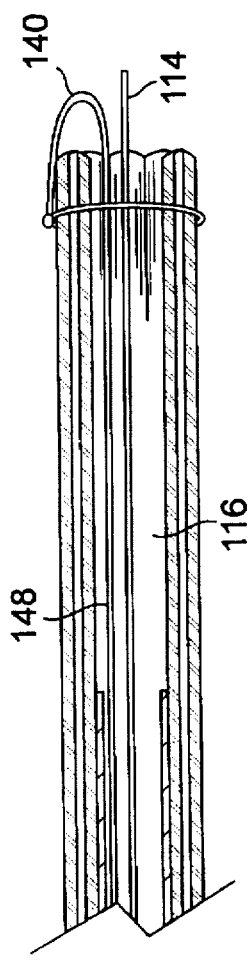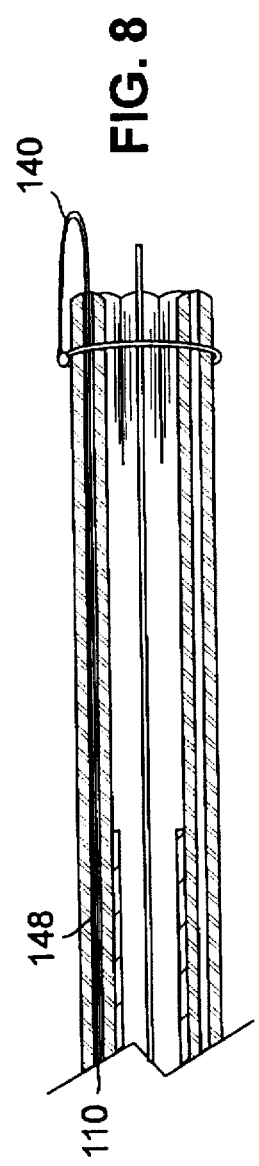

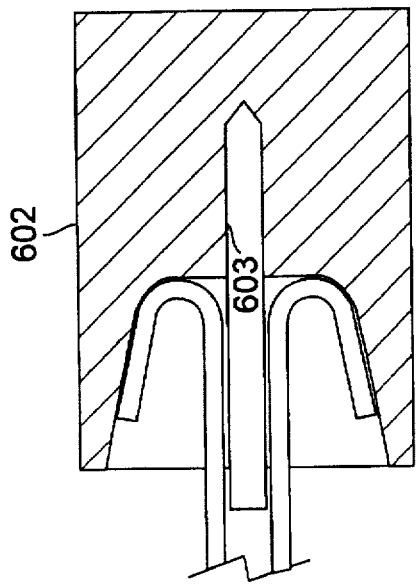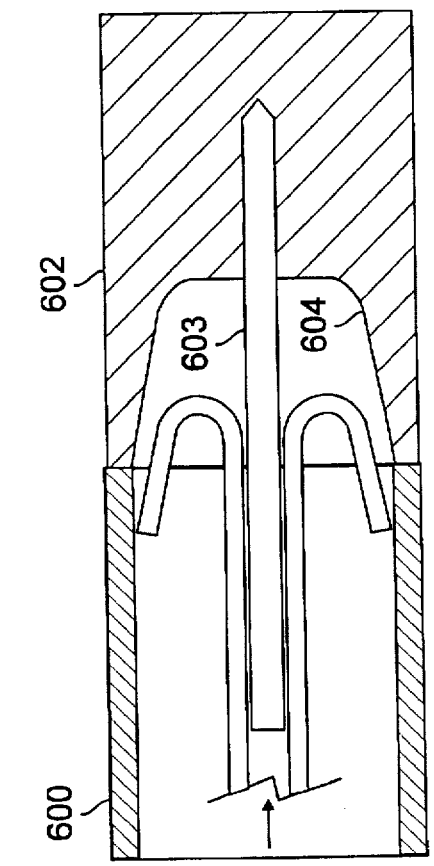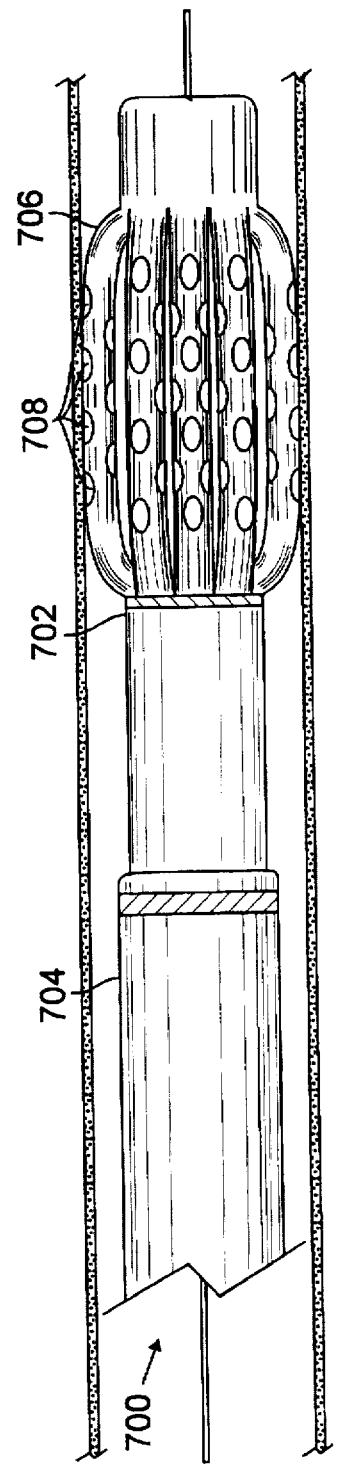
FIG. 23
FIG. 22B
FIG. 24

METHODS FOR TREATING THROMBOSIS

FIELD OF THE INVENTION

A drug delivery catheter and, more particularly, a drug delivery catheter with a self-expanding drug delivery portion which delivers drugs or other agents proximate the walls of a lumen or vessel, such as an artery or vein, and methods of its use.

BACKGROUND OF THE INVENTION

It is often necessary to deliver drugs to a particular site within a body. For example, catheters are used to deliver drugs or other agents to lumens or vessels within the cardiovascular system, the urethra, bladder, prostate, rectum and central nervous system, such as the spinal cord.

In cardiovascular applications, for example, various types of agents are being investigated for use in preventing restenosis of an artery after percutaneous transluminal coronary angioplasty (PTCA) or percutaneous transluminal angioplasty (PTA). Heparin, an anticoagulant and inhibitor of arterial smooth muscle proliferation, is one such drug. Dexamethasone may also prevent smooth muscle proliferation. Integralin, an antiplatelet agent, can also be useful to prevent restenosis. See, for example, "Use of a Monoclonal Antibody Directed Against the Platelet Glycoprotein IIb/IIIa Receptor in High-Risk Coronary Angioplasty," Califf, Dr. Robert M., The New England Journal of Medicine, Apr. 7, 1974, p. 956. Other drugs and agents are being investigated for efficacy, as well. Such drugs can be delivered before or after the angioplasty procedure. The delivery of lytic agents such as urokinase, streptokinase and recombinant tissue type plasminogen activator (rTPA), to dissolve plaque or a thrombosis in arteries and veins is also being investigated. Integralin may be efficacious, as well.

Because of blood flow through the artery, drugs delivered to the site of an angioplasty procedure, for example, can be rapidly dissipated and removed from the delivery site before they can be absorbed in sufficient quantities to become effective. Catheters have therefore been developed to directly deliver drugs to the desired site and maintain them there. For example, U.S. Pat. No. 5,087,244 to Wolinsky et al., discloses a catheter with a flexible balloon having a plurality of minute openings. The balloon can be inflated by heparin. As the walls of the balloon contacts the arterial wall, the heparin exits the balloon, directly onto the walls. While enabling drug delivery directly to the desired site, the inflation of the balloon can damage the arterial wall, promoting restenosis. The balloon can also block the perfusion of blood distal to the delivery site, depriving tissue of needed blood. This limits the amount of time available for drug delivery. In addition, since the balloon is inflated by the heparin, heparin can leak out before the arterial wall is contacted, wasting the drug. The balloon also needs to be deflated prior to removal or to allow blood flow. The pressure required to deflate the balloon could draw blood into the balloon, preventing further use of the catheter until the blood has been removed.

U.S. Pat. No. 4,824,436, also to Wolinsky, discloses a drug delivery catheter comprising a pair of occlusion balloons for securing the catheter in position and isolating a region of the artery which has been opened by PTCA, and a drug delivery conduit for delivering heparin under pressure into the region isolated by the occlusion balloons. The pressure of the heparin forces the heparin to coat to and penetrate the arterial tissue. This configuration presents the similar perfusion problems to those discussed above. The heparin, therefore, is only delivered for 5–60 seconds, which may be inadequate for sufficient absorption.

In U.S. Pat. No. 4,636,195, Wolinsky discloses a similar catheter for delivering a solubilizing solution for dissolving plaque blocking an artery. This patent also relies on the pressure of drug delivery to force the solution into the plaque. A third balloon can also be provided between the two occlusion balloons to compress the plaque and force the solubilizing solution into it. The solution can be delivered at a low pressure and absorb passively, as well.

The use of sufficient pressures to drive the drug into the tissue or plaque may damage the arterial wall. Passive delivery is slow and may not enable sufficient absorption of the medication. Passive delivery can be particularly inappropriate for drug delivery in an artery because of the limited time blood flow can be stopped.

U.S. Pat. No. 5,336,178 to Kaplan et al., discloses a catheter with drug delivery ribs which are brought into contact with the walls of the body lumen by an inflatable balloon. A series of ports in the catheter shaft can be provided proximal to the balloon, to allow for perfusion of blood through the catheter shaft. As above, the amount of blood which can be perfused is limited. Inflation of the balloon can also damage the wall of the lumen.

One commercially available drug delivery product is the DISPATCH™ from Scimed®. The DISPATCH™ includes an inflatable polyurethane coil which provides a path for blood to flow and defines regions proximate the wall of the vessel into which drug is delivered. While apparently allowing for significant perfusion, the device is complex and difficult to use and manufacture. The inflatable coil can also prevent portions of the artery from being exposed to the drug.

Active perfusion, such as the injection of perfluorochemicals or blood through the guide wire lumen, is also used.

It is known that the velocity of fluid flow through a tube varies across the axial cross-section of the tube. The velocity is maximum at the center of the tube and approaches zero at the walls. In an artery or a vein, blood flow is very slow in the region proximate the walls. If drugs or other agents could be effectively delivered proximate the walls, the blood or other fluid flow can atraumatically carry the delivered drug or agent over the site of interest. The delivered drug or agent would also not dissipate as rapidly as drug delivered at the center of the vessel. Less drug could then need to be delivered, shortening procedures and decreasing their cost.

A drug delivery device which could deliver drugs proximate the walls of the vessel without blocking blood flow, would be advantageous.

SUMMARY OF THE INVENTION

A catheter is disclosed comprising self-expandable delivery members which are compressed while the catheter is advanced to a site within a lumen, such as an artery or a vein, for example. When released at a desired site, the delivery members flare toward the wall of the lumen to deliver drugs or other agents proximate the wall.

In accordance with one embodiment of the invention, a catheter is disclosed comprising a delivery portion comprising a shaft, at least one resilient delivery member at the distal portion of the shaft, and at least one delivery lumen extending longitudinally through the shaft and delivery member. The delivery member includes at least one delivery port in fluid communication with the delivery lumen. The delivery member is capable of extending from the shaft at an angle with respect to a longitudinal axis through the catheter shaft. A means for compressing the delivery member is also provided, wherein when the means for compressing is removed from the delivery members, the delivery members flare to the angle with respect to the catheter shaft.

In accordance with another embodiment of the invention, a catheter is disclosed comprising a shaft having distal and proximal portions, and a sleeve, wherein the shaft is received within the sleeve and the shaft and sleeve are adapted to be moved with respect to each other. The shaft comprises a plurality of resilient delivery members extending from the distal portion of the catheter shaft at an acute angle with respect to a longitudinal axis of the catheter shaft when the sleeve is retracted from the distal portion. The delivery members are compressed by the sleeve when the distal portion of the shaft is received within the sleeve. A plurality of delivery lumens corresponding to the number of delivery members extend through the catheter shaft and delivery members. At least one delivery port is provided in each delivery member.

A catheter is also disclosed comprising a shaft having distal and proximal portions, and a sleeve, wherein the shaft is received within the sleeve and the sleeve and shaft can move with respect to each other. The shaft comprises a plurality of resilient delivery members flaring from the distal portion of the shaft at an acute angle with respect to a longitudinal axis of the catheter shaft when the sleeve is retracted from the distal portion. The delivery members comprise a first, tapered portion having a distal end and extending at the angle with respect to the longitudinal axis of the catheter shaft, and a second, essentially longitudinal portion depending from the distal end of first portion. A plurality of delivery lumens corresponding to the number of delivery members extend through the shaft and delivery members. At least one delivery port is provided in each delivery member.

A catheter is also disclosed comprising a shaft having distal and proximal portions, and a sleeve, wherein the catheter shaft is received within the sleeve and the sleeve and shaft can move with respect to each other. The shaft comprises a plurality of resilient delivery members having a first portion with a distal end extending rearwardly from the distal portion of the shaft when the sleeve is retracted from the distal portion. The shaft further comprising a plurality of delivery lumens extending through the shaft and the delivery members.

A catheter is also disclosed wherein the delivery members are compressed by a thread. When the thread is removed, the delivery members flare from the catheter shaft at an angle with respect to a longitudinal axis of the catheter shaft.

In all the above embodiments, the delivery members are preferably adapted to bear against the wall of a lumen when released at a site. Different drugs or other agents can be delivered through different lumens.

A method of delivering drugs or other agents to a lumen is also disclosed comprising advancing a catheter having compressed delivery members, releasing the delivery members, and delivering drugs or other agents through the catheter and delivery members.

A method of treating thrombosis is also disclosed comprising advancing a first catheter with compressed delivery members proximal to a thrombus, advancing a second catheter with compressed delivery members through the thrombus, releasing the delivery members of the first catheter, releasing the delivery members of the second catheter, delivering drugs or other agents through the first catheter, and delivering drugs or other agents through the second catheter.

A method is also disclosed comprising advancing a distal portion of a catheter having compressed expandable solid members through a thrombus, releasing the solid members to extend rearwardly from a distal end of the catheter, and removing the thrombus by retracting the catheter into a guide catheter, for example.

DESCRIPTION OF THE FIGURES

FIG. 1 is a side view of a drug delivery catheter in accordance with a first embodiment of the invention in its deployed position within a lumen, such as an artery;

FIG. 2 is a partial cross-sectional view of the catheter of FIG. 1, with a sleeve partially cut away to reveal the distal portion of the shaft, when the catheter is in a non-deployed position;

FIG. 3 is a cross-sectional view of the catheter of FIG. 1;

FIG. 4 is a cross-sectional view of the catheter of FIG. 1, through line 4—4 of FIG. 1;

FIG. 5 is a cross-sectional view of the proximal portion of the catheter of FIG. 1;

FIG. 6 is a cross-sectional view of the catheter of FIG. 1, wherein a thread compresses the delivery members;

FIG. 7 is a cross-sectional view of the catheter of FIG. 1, wherein the thread extends through a guide wire lumen;

FIG. 8 is a cross-sectional view of the catheter of FIG. 1, wherein the thread extends through a delivery lumen;

FIGS. 20–23 illustrate steps in the manufacture of the catheter of FIG. 16;

FIG. 24 is a side view of a fourth embodiment of a catheter in its deployed position within a lumen such as the vena cava;

DESCRIPTION OF THE INVENTION

Figure 9A:
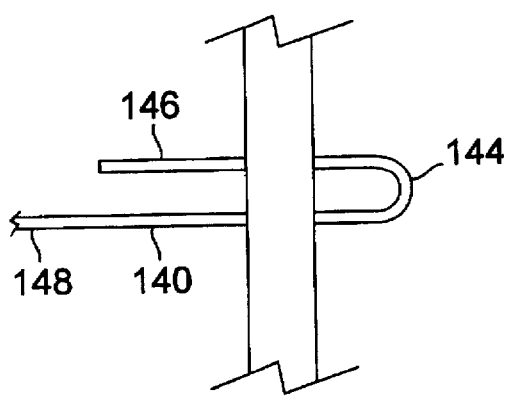
FIGS. 9A–9E illustrate the formation of a releasable knot for use with the embodiments of FIGS. 6–8.
Figure 9B:
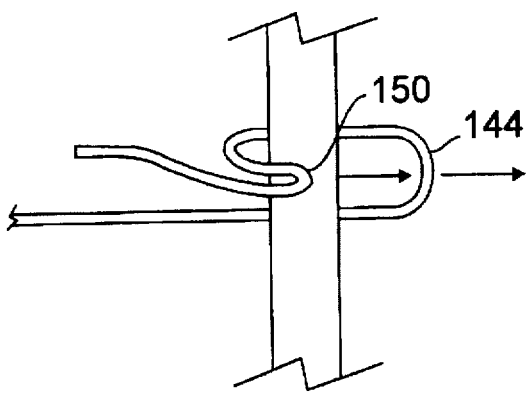
Figure 9C:
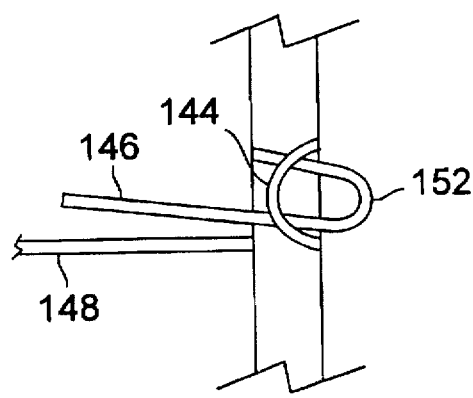
Figure 9D:
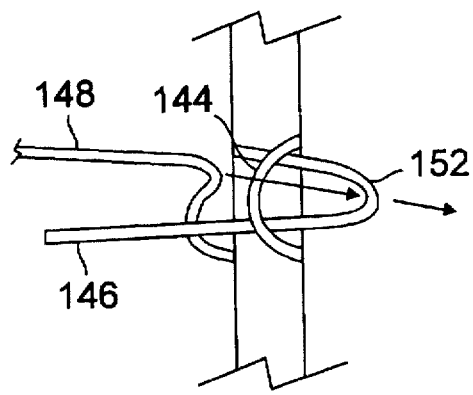
Figure 9E:
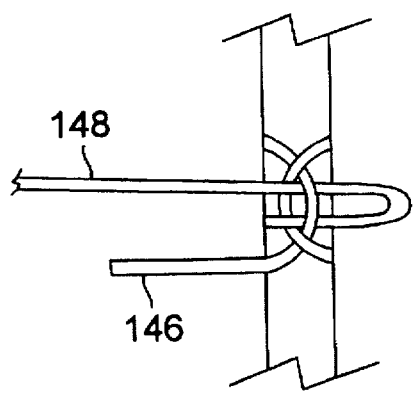

FIG. 1 is a side view of a catheter 100 in accordance with one embodiment of the present invention, deployed to deliver drugs or other agents in a lumen or vessel, such as an artery 102. The catheter comprises a shaft 104 with a distal portion comprising one or more resilient delivery members 106 which flare from the shaft at an acute angle, towards the walls of the artery 102. Eight delivery members 106 are provided in this embodiment, five of which are shown in FIG. 1. The three additional delivery members, obscured in the view of FIG. 1, are shown in FIG. 2.

FIG. 2 is a view of the catheter 100 of FIG. 1, in a position prior to deployment. A means is shown in FIG. 2 compressing the resilient delivery members 106. The means is preferably a member, such as a sleeve 108, a portion of which is shown in cross-section in the view of FIG. 2. The sleeve 108 preferably extends over the length of the shaft 104. The sleeve 108 compresses the delivery members 106, maintaining them within the inner diameter of the sleeve 108 while the catheter 100 is stored, advanced to a desired site and, optionally, when the catheter 100 is withdrawn. When the distal end of the catheter 100 is properly positioned at the site of interest B, the delivery members 106 can be released by retracting the sleeve 108, allowing the delivery members 106 of the distal portion to flare outward beyond the outer diameter of the shaft 104 and sleeve 108, to preferably contact and bear against the lumen walls, as in FIG. 1. This ensures that the drug is delivered proximate the wall.

The means for compressing need only extend over the distal portion of the shaft 104 or over the delivery members 106 themselves. A ring, collar, short sleeve or thread can also be used to compress the members. Thread, tubes or rods, for example, can also be coupled to the means for compressing, to withdraw the means for compressing from the delivery members 106. An embodiment using thread to compress and release the delivery members is discussed in conjunction with FIGS. 6–9, below.

Drugs or other agents are delivered through delivery lumens 110 extending longitudinally through the shaft 104 and delivery members 106, as shown in FIG. 3, to ports 112 preferably located at the distal ends of the delivery members 106. The ports 112 deliver the drug proximate the wall of the artery where the fluid flow is very slow. A guide wire 114 and a guide wire lumen 116 extending longitudinally through the shaft 104 are also shown in this view.

Preferably, the drug is delivered upstream of the site with respect to the blood flow so that the slow blood flow proximate the wall atraumatically carries the drug over the site. In FIG. 1, the direction of blood flow is indicated by an arrow A and the site is indicated by B.

FIG. 4 is a cross-sectional view of the catheter of FIG. 1 along line 4—4. The guide wire lumen 116 and the eight drug delivery lumens 110, one for each delivery member 106, are shown. The same drug or agent can be delivered through all eight lumens and members, or different drugs or agents can be delivered through some or all of the lumens and members. While the term "drug" is generally used hereafter, it is understood that other agents can be delivered as well.

The number of delivery members 106 can vary. The preferred number can depend on the diameter of the vessel where the drug is to be delivered. For example, eight delivery members 106 are preferably provided in this embodiment, which will enable an even distribution of the delivered drug around the circumference of the arterial wall in an artery with a diameter of between about 2.5–5 mm.

Additional delivery members 106 could be preferred for larger vessels, while fewer can be used in smaller vessels. The delivery members 106 are preferably integral portions of the catheter shaft 104, and are of the same polymeric material as the shaft 104.

As mentioned above, the delivery members 106 preferably bear against the wall of the lumen when fully deployed to ensure drug delivery proximate the walls of the artery. The force with which the members 106 bear against the wall also prevents the members 106 from being displaced from the walls of the artery, or other such lumen, by blood or fluid flow. In coronary arteries, the pumping of the heart could also displace the members. The bearing force is insufficient to damage the walls of the vessel.

To provide such a stabilizing, bearing force, the delivery members 106, when fully extended, preferably have an outermost diameter D, measured across a circumference defined by the outer tips of the members, as shown in FIG. 3, slightly greater than the diameter of the vessel. The delivery members 106 preferably extend from the shaft at an angle of between about 25°–50° when fully deployed. The wall of the vessel or lumen preferably compresses the delivery members 10–50% from their fully flared positions. The lesser of 10% or 0.4 mm compression of the diameter is most preferred. Preferably, the ratio between the diameter D when fully flared and the horizontal distance H from the shaft 104 to a projection of the tip of the member to the longitudinal axis, is between about 2:1 to 1:1, to achieve sufficient bearing force against the lumen wall.

For example, the diameters of the arteries can vary between about 2.5–8.0 mm. If the catheter is intended for use in an artery with a diameter of about 3.0 mm, the delivery members are preferably configured to have an outer diameter D of about 3.3 mm when fully extended. If the members 106 flare from the shaft 104 at an angle of about 45°, the length L of the members 106 would be about 2.3 mm. For use in a larger artery, with an inner diameter of about 8 mm, for example, the diameter D between opposing members can be about 8.4 mm. If the members 106 flare from the shaft 104 at an angle of about 45°, the length of each member 106 is about 6 mm.

The inner diameters of the delivery lumens 110 and their ports 112 are preferably between about 0.005–0.010 inches. If greater drug delivery is desired, larger delivery lumens 110 can be provided.

The diameters of the shaft 104 and sleeve 108 may vary dependent upon the diameter of the intended site. For example, in regions of arteries having diameters of between about 2.5–5 mm, the outer diameter of the sleeve 108 can be about 0.065 inches or less. The inner diameter of the sleeve 108 is preferably about 0.055 inches. The outer diameter of the shaft 104 can be about 0.045 inches. Clearance 117 is preferably provided between the sleeve 108 and the shaft 104 to ease the movement of one with respect to the other, as shown in FIGS. 2–4. A larger diameter catheter may be desired for a site with a larger diameter while a smaller diameter catheter may be used for a narrower site. The diameter of the guide wire lumen 116 can be about 0.022 inches, for example.

When flared, the drug delivery members 106 are separated by sufficient space to allow for significant perfusion of blood between the members. This increases the possible length of surgical procedures, without requiring perfusion means which can increase the complexity of the use and manufacture of the catheter.

Returning to FIG. 1, the sleeve 108 preferably includes a radiopaque band 118 of gold or tantalum, for example, at its distal end, to assist in tracking the progress of the catheter on a fluoroscope during a procedure. The shaft 104 also preferably includes a radiopaque band 120, preferably just proximal to the point where the delivery members 106 separate from the shaft 104. The bands 118, 120 are preferably positioned such that when the radiopaque band 118 of the sleeve 108 is essentially aligned with the radiopaque band 120 of the shaft 104, the sleeve 108 has been sufficiently retracted to release the delivery members 106, as shown in FIG. 3. The sleeve 108 may be further retracted from the distal end of the shaft 104 during use, as well.

The sleeve 108 and shaft 104 preferably comprise materials which will easily slide with respect to each other. The shaft 104 is also preferably a thermoplastic elastomer with shape memory capability with proper processing, as described below. The shaft 104 can be a thermoplastic elastomer resin such as a polyether block amide (PEBA). PEBAX®, available from Atochem Inc., N.J., is one such material. A hardness of between about 25–50 Shore D is preferred for the shaft 104, with a hardness of 40 most preferred. The characteristics of an appropriate material, PEBAX® grade 4033 SA 00, for example, appear below:

| Hardness | |
| --- | --- |
| Shore D | 40 |
| Shore A | 90 |
| Melt Flow Rate ASTM D1238 Q 2 mm orifice | 3–7 |
| Water Absorption 24 hours ASTM D 570 Equilibrium 20° C./65% RH | 1.2% 0.5% |
| Elongation ASTM D638 At Break | 485% |
| Tensile strength ASTM D638 At Break | 36 MPa 5220 psi |
| Flexural Modulus ASTM D790 | 75 MPa 10,900 psi |
| Maximum Flexure ASTM D790 | 27 mm 1.06 inches |
| Stress ASTM D790 | 4.3 MPa 624 psi |
| Resilience BS 903 Part 08 Method A | 62.5% |
| Melting Point (Optical) ASTM D2117 | 168° C. 334° F. |
| Melting Range DSC ASTM D3418 | 119–170° C. 246–338° F. |
| Vicat Softening Point ASTM D1525 | 132° C. 270° F. |

Hytrel®, a polyester elastomer available from Du Pont, Wilmington, Del., and all the known grades of polyethylene, such as linear low density polyethylene (LLDPE), low density polyethylene (LDPE), high density polyethylene (HDPE) and ultra high density polyethylene (UHDPE), and other thrombogenic materials which are appropriate for catheter shafts and can exhibit shape memory characteristics, can be used, as well.

An appropriate material for the sleeve 108 is Marlex HHM 4903 HDPE, for example, available from Phillips 66, Pasadena, Tex. Characteristics of Marlex HHM 4903, appear below:

| Melt Index Condition 190/2.16 D1238 | 0.30 g/10 min |
| --- | --- |
| Tensile Yield Strength 2 in. (50 mm) per min. D638 Type IV | 3600 psi 25 MPa |
| Ultimate Elongation 2 in. (50 mm) per min. D638 Type IV | >600% |
| Flexural Modulus D790 | 170 psi 1171 MPa |

Another appropriate material for the sleeve 108 is Hytrel® 5556. It may be desirable when using Hytrel® 5556 to provide a distal portion of the shaft of a softer material, such as Hytrel® 4056, for improved flexibility and to prevent tissue damage. Characteristics of Hytrel® 5556 and 4056 appear below:

| | 5556 | 4056 |
| --- | --- | --- |
| Hardness D2240 | 55 Shore D | 40 Shore D |
| Melting Point Peak of Endotherm Melt Complete D3418 | 201° C. 220° C. | 145° C. 170° C. |
| Tensile Strength D638 | 44 MPa | 30 MPa |
| Ultimate Elongation D638 | 560% | 560% |
| Flexural Modulus D790 | 207 MPa | 48 MPa |
| Resilience Bashore | 53% | 62% |
| Compression Set 22 hours at 70° C. Constant Load (9.3 MPa) D395A | 4% | 27% |
| Vicat Softening Point D1525 | 180° C. | 112° C. |

Other non-thrombogenic materials can be used as well. For example, the sleeve 108 can comprise PEBAX®, with a hardness of 55, for example, polytetrafluoroethylene (PTFE), polyethylene, fluorinated ethylene propylene (FEP), and all the known grades of polyethylene such as LLDPE, LDPE, HDPE and UHDPE.

To further ease movement of the sleeve 108 with respect to the shaft 104, a lubricous coating of silicone, for example, is provided over the shaft 104. To ease transport through the guide catheter and in the vessel, the lubricous coating is preferably provided over the sleeve 108, as well.

If the preferred materials for the sleeve 108 and shaft 104 are not rigid enough to be easily advanced along the guide wire 114 through a guide catheter, a reinforcing sleeve 122 of stainless steel, titanium, or titanium nickel, for example, may be provided within the guide wire lumen 116, as shown in FIGS. 3–5. The reinforcing sleeve 122 preferably extends from the proximal end of the catheter 100, more than half the length of the catheter 100, up to about 12 inches or about 30 mm from the distal end of the shaft 104. Where the guide wire lumen 116 is about 0.022 inches, the reinforcing sleeve 122 can have an outer diameter of about 0.020 inches and an inner diameter of about 0.016 inches, for example.

Other means of reinforcing the catheter can be used as well. For example, the sleeve 108 can be reinforced instead of the shaft 104. A rigid wire or stylet can also be embedded within the sleeve 108 or shaft 104. Irradiation of the sleeve or shaft with an electron beam to increase the cross-linking and hence the stiffness of the polymeric material, can also be used, as is known in the art. A harder material can also be used for the sleeve 108 or shaft 104 than those preferred above, in which case the distal portion of the sleeve or shaft may need to be "necked down" to decrease its outer diameter, increasing its flexibility.

The catheter 100 of the present invention can be used to deliver antiproliferatives, anticoagulants, or antiplatelet agents, such as heparin, dexamethasone, and Integralin, to the site of a PTCA, PTA or stent procedure to prevent restenosis, for example. The drug can be delivered before or after the dilatation procedure. It can also be used to deliver lytic agents, such as urokinase, streptokinase or rTPA to the site of a thrombus in an artery or vein. A preferred configuration for use in a vein is shown in FIGS. 16–19, and described further below. Other drugs and agents known or to be developed, could be delivered, as well.

FIG. 5 is a cross-sectional view of the proximal portion of the catheter 100, including a manifold 124 for providing a drug or other agent into the delivery lumens 110. The drug is supplied from a drug infusion unit 126 or a syringe (not shown) through a first port 128. The guide wire 114 can extend through a second port 130. A ring 132 at the proximal end of the catheter 100 is attached to the sleeve 108 to advance or retract the sleeve. The sleeve 108 is retracted by withdrawing the ring 132 a sufficient distance so that the distal portion of the sleeve 108 is no longer compressing or restraining the delivery members 106. Advancing the ring 132 advances the sleeve 108 back over the delivery members 106.

A seal, such as an O-ring 133 of latex or silicone, for example, is provided between the ring and proximal portion of the catheter shaft 104 to prevent leakage. A port 135 can be provided through the ring 132 to enable venting of air. Saline may also be delivered through the port 135 to maintain the clearance 117 open. The port 135 could also be used to delivery a drug or other agent, such as heparin, into the vessel. The manifold 124 can be easily modified to deliver different drugs or other agents through different ports, as well.

In use, the catheter 100 of the invention can be advanced to the site of interest B over the guide wire 114 through a guide catheter (not shown). The delivery members 106 are preferably positioned such that drug will be delivered upstream of the site of interest with respect to the blood flow. For example, if the catheter 100 is advanced along the direction of blood flow, the drug delivery would preferably be proximal to the site B, as in FIG. 1. If the catheter 100 is advanced in a direction opposing the blood flow, the drug delivery would preferably be distal to the site, as in FIG. 16.

When the catheter 100 is properly positioned, the sleeve 108 is retracted by withdrawing the ring 132 a sufficient distance. Preferably, this can be observed by the alignment of the radiopaque bands 118, 120 on the shaft 108 and sleeve 104, as shown in FIG. 3. The delivery members 106 would then rotate through an acute angle, to the position of FIG. 1. The drug or other agent is then delivered proximate the vessel wall. The slow blood flow proximate the vessel wall will atraumatically carry the delivered drug over the site B. Perfusion of blood is not impeded, as blood or other fluids will flow between the delivery members. If desired or necessary, the sleeve 108 can be retracted further than shown in FIGS. 1 or 3.

When sufficient drug has been delivered, the sleeve 108 can be advanced back over the distal portion of the shaft 104 or the shaft 104 can be withdrawn into the sleeve 108. The catheter 100 can then be removed through the guide catheter. It is also possible to remove this embodiment of the invention through the guide catheter while it is in the deployed position. In addition to delivering drugs through the members, the guide wire 114 can be removed and drugs can be delivered through the guide wire lumen 116. This could be particularly useful in the treatment of thrombosis, where the drug can be directed toward the center of the thrombus, as well as its periphery along the wall of the vessel. In addition, while the drug is preferably delivered proximate the wall of the vessel or lumen, drug can be delivered at various locations across the cross-section of the vessel by varying the degree to which the sleeve is retracted. Drugs can also be delivered through port 135, of FIG. 5, through the clearance 117 between the sleeve 108 and shaft 104.

FIGS. 6–9 show a variation in the embodiment of FIGS. 1–4, wherein instead of a sleeve 108, a thread 140 restrains and compresses the delivery members 106. The thread 140 can be tied around the periphery of the delivery members 106, in a releasable knot 142, such as a horse thief's knot, shown in FIG. 9E. Formation of a horse thief's knot is shown in FIGS. 9A–9D. First, a loop 144 is formed at one end of the thread 140, beneath the delivery members 106. For illustrative purposes, the delivery members are not shown in these views. The loop 144 has a short end 146 and a long end 148. A portion 150 of the short end 146 is carried over the members and beneath the loop 144 as shown in FIG. 9B, to form a second loop 152, as shown in FIG. 9C. The long end 148 is then carried under the short end 146, over the first loop 144 and through the second loop 152. The short end 146 is pulled to tighten the knot. Pulling the long end 148 releases the knot, allowing the delivery members 106 to flare to their deployed position.

The long end 148 of the thread 140 can extend over the exterior of the shaft 104 as shown in FIG. 6, through a lumen within the shaft 104, such as the guide wire lumen 116, as shown in FIG. 7 or through a delivery lumen 110 as shown in FIG. 8. The guide wire lumen 116 can be divided into two lumens, one for the guide wire 144 and one for the thread 140. The thread 140 can be nylon, for example. The thread can have a diameter between about 0.005–0.008 inches, for example. The use of a thread 140 instead of a sleeve decreases the outer diameter of the catheter and may therefore be particularly suited for use in small vessels, such as cerebral arteries which can have diameters of about 1.0–2.5 mm, for example. The proximal portion of the catheter as shown in FIG. 5 can be suitably modified for use with this embodiment. For example, no ring 132 is required to retract a sleeve.

Figure 10:
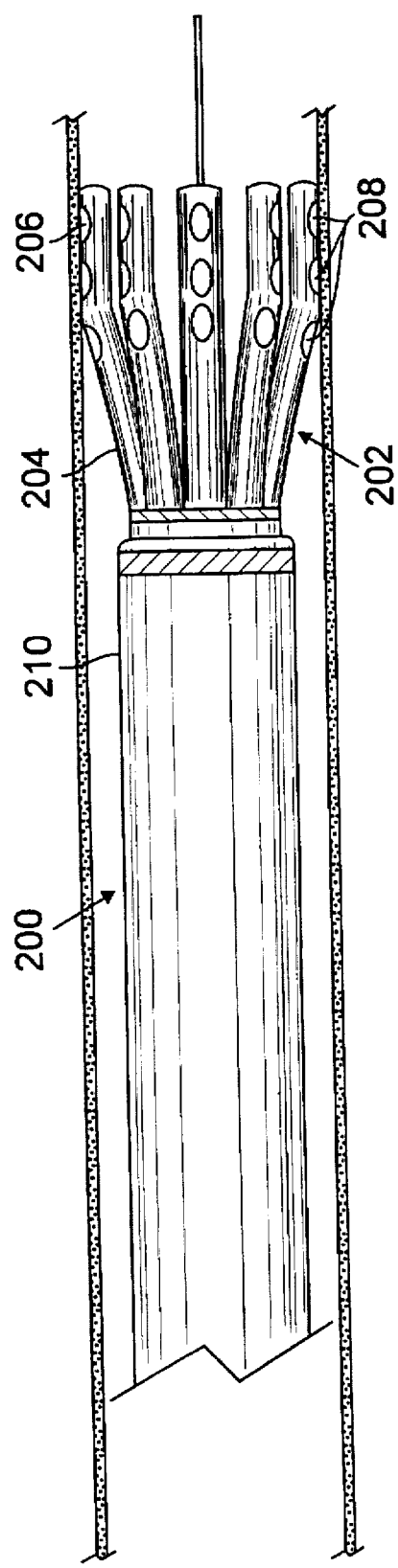
FIG. 10 is a side view of a catheter of a second embodiment of the present invention, in its deployed position within a lumen.

FIG. 10 shows a catheter 200 in accordance with a third embodiment of the invention wherein the delivery members 202 comprise a first, tapered portion 204 and a second, longitudinal portion 206. A series of ports 208 can be provided along the tapered and longitudinal portions for delivering drug proximal to the site of interest. A single port can be provided at the distal end of the member, as in the embodiment of FIG. 2, as well. The drug can also be delivered directly onto the site of interest. The ports 208 can have a diameter of about 0.005–0.010 inches. The remainder of the catheter 200 is the same as above.

Figure 11:
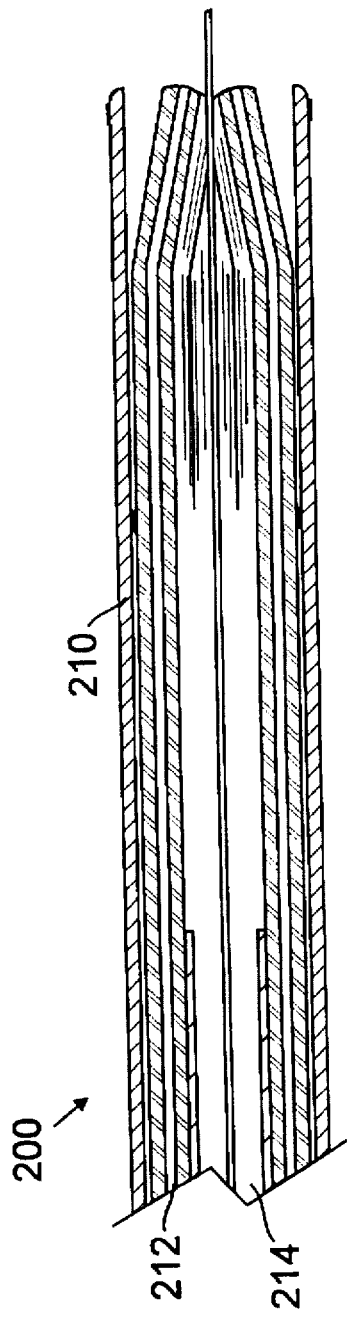
FIG. 11 is a cross-sectional view of the catheter of FIG. 10.

FIG. 11 is a partial cross-sectional view of the catheter 200 wherein the delivery members 202 are within and compressed by a sleeve 210. The sleeve 210 is shown in partial cross-section in this view. Delivery lumens 212 and guide wire lumen 214 are shown as well. The delivery members 202 can be compressed by a thread, as in FIGS.

7-9, or other compressing means, as well. The proximal portion of the catheter 200 can be the same as that shown in FIG. 5.

To manufacture the catheters of the embodiments of FIGS. 1-9, in accordance with the present invention, the shaft 104 can be extruded in a multi-lumen extrusion process, as is known in the art. One or both ends of the extrusion can have a tapered portion leading to a wider longitudinal region, to ease subsequent operations on the shaft. Such wider regions can be formed by a bump extrusion process, also known in the art.

The delivery members 106 are formed by cutting the distal end of the shaft 104 between each of the delivery lumens 110 a desired length depending on the desired length for the members. A blade or other thin cutting surface is preferred. The shaft can be cut by hand or by a machine. The machine can include a mounting for securing the shaft and a series of cutting blades disposed radially to simultaneously cut the distal portion of the shaft along its longitudinal axis. The number of blades corresponds to the number of delivery members desired. The thickness of the blades is preferably less than 0.010 inches. A thickness of about 0.005 inches or less is most preferred. If a bump extrusion is used to form the distal end, the distal end is cut through the taper to shorten that end, before cutting the shaft. The shaft can be cut with a laser, as well.

As mentioned above, the length of the delivery members 106 can vary depending on the application. The length of all the delivery members is preferably the same, which enhances the ability of the members to deploy after retraction of the sleeve.

Figure 12:
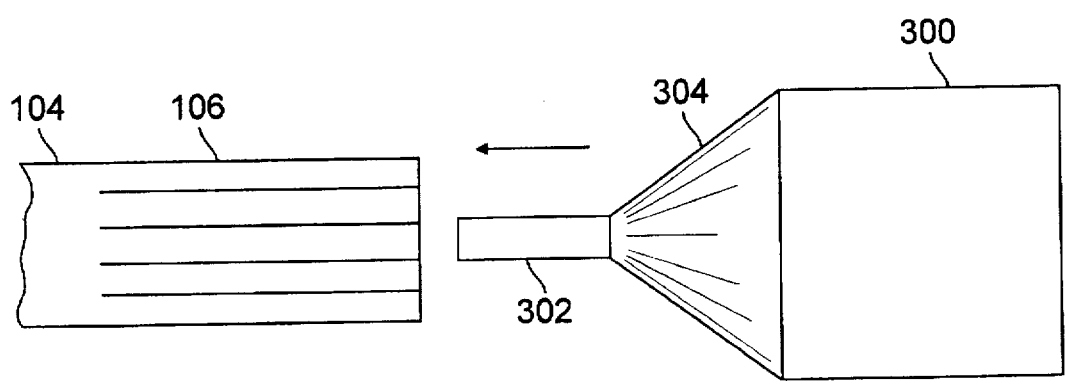
FIGS. 12–13 illustrate steps in the manufacture of the catheters of FIGS. 1 and 10.
Figure 13:
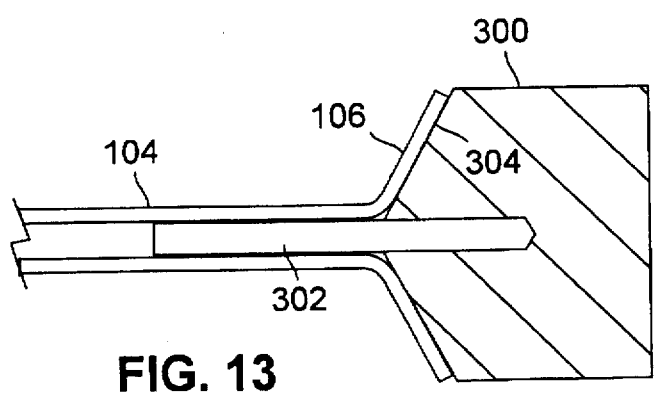

To form the flare in the embodiment of FIGS. 1-6, a tool, such as the tool 300 shown in FIG. 12, is inserted within the guide wire lumen 114 of the extruded shaft 104, after the distal portion is cut, as shown in FIG. 12. The tool 300 comprises a rod shaped guiding mandrel or wire 302 depending from a conical surface 304. As the distal ends of the delivery members 106 engage the conical surface, they are forced outward, as shown in the cross-sectional view of FIG. 13. The tool 300 is advanced to the uncut portion of the shaft. When the tool 300 is suitably positioned, the shaft 104 and tool 300 are placed in an oven at about 225°–250° F. for about 5-30 minutes, to heat set the delivery members 106. In this embodiment, the angle of the flare is preferably between about 250°–50°. If the bump extrusion process is used for the distal end, the delivery members 106 will already be partially tapered. The extent of additional flaring after cutting may not then be as great. The tool 300 can be made of brass, stainless steel or PTFE, for example.

After heat setting, the reinforcing sleeve 122 is inserted into the shaft 104. Radiopaque bands 118, 120 are preferably applied to the shaft 104 and sleeve 108. A lubricous coating is applied to the shaft 104 and the sleeve 108 is placed over the shaft 104 or the thread 140 is tied to the delivery members 106.

Figure 14:
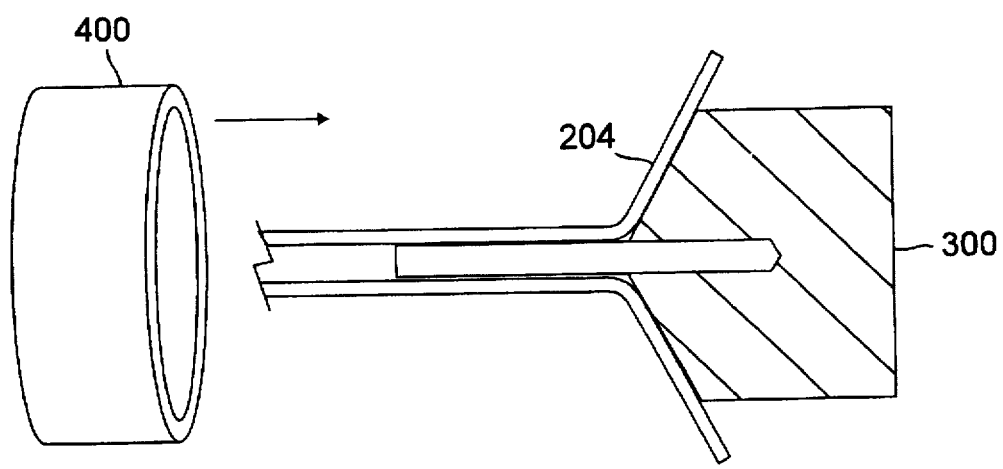
FIGS. 14–15 illustrate further steps in the manufacture of the catheter of FIG. 10.
Figure 15:
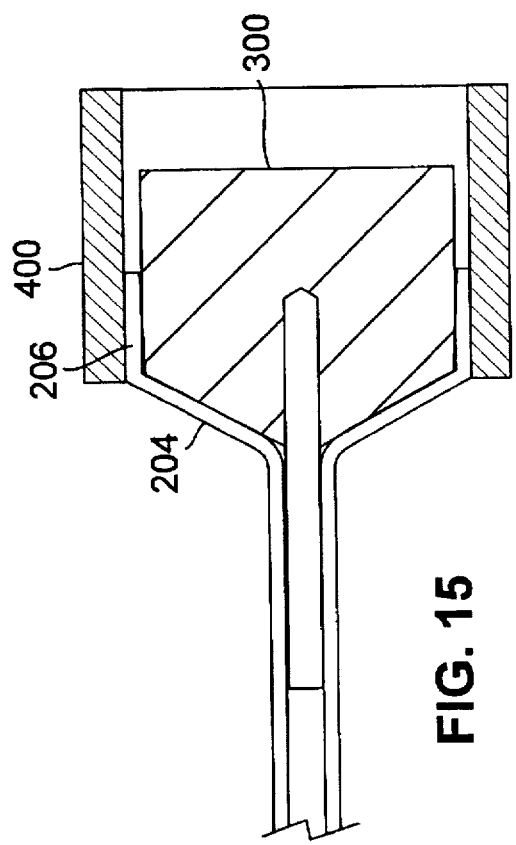

In manufacturing the embodiment of FIGS. 10-11, wherein the delivery members 202 include the second, longitudinal portion 206, the distal end of the shaft is preferably not bump extruded. The first, flared portion of the delivery members 106 can be formed with the same tool as used in the first embodiment. The tool 300 is advanced until the members 202 extend beyond the conical portion of the tool the desired length of the first longitudinal portion 206, as shown in FIG. 14. A tube or collar 400 with a diameter slightly greater than the diameter of the tool 300, is then passed over the proximal end of the shaft, and over the first tool 300, ensuring that the delivery members 202 bear against the wall of the first tool 300, as in the cross-sectional view of FIG. 15. The shaft is then heated, as above. The ports can be formed by a punch, drill or laser, as is known in the art.

FIGS. 16-19 show another embodiment of the present invention, particularly suited for use in a vein, such as the inferior vena cava, or in cerebral arteries. The catheter 500 is the same as the catheter 100 in FIGS. 1-6, except that the delivery members 502 extend rearwardly from the distal end of the shaft 504, as shown in the side view of FIG. 16. The delivery ports 506 are preferably located at the end of the delivery members 502. A plurality of ports can be provided along the inside surfaces of the delivery members 502, as well. This configuration is preferred for delivering drugs or other agents in a vein because in such applications, the catheter is typically inserted into the jugular or femoral vein, in a direction opposite the blood flow, indicated by arrow C in FIG. 16. This configuration delivers the drug or other agent proximate the vessel wall, in the direction of the blood flow. The blood then slowly carries the delivered drug atraumatically across the intended site, indicated by E. Delivery in a direction opposite the blood flow could cause eddy currents, preventing laminar flow along the vessel wall.

Figure 16:
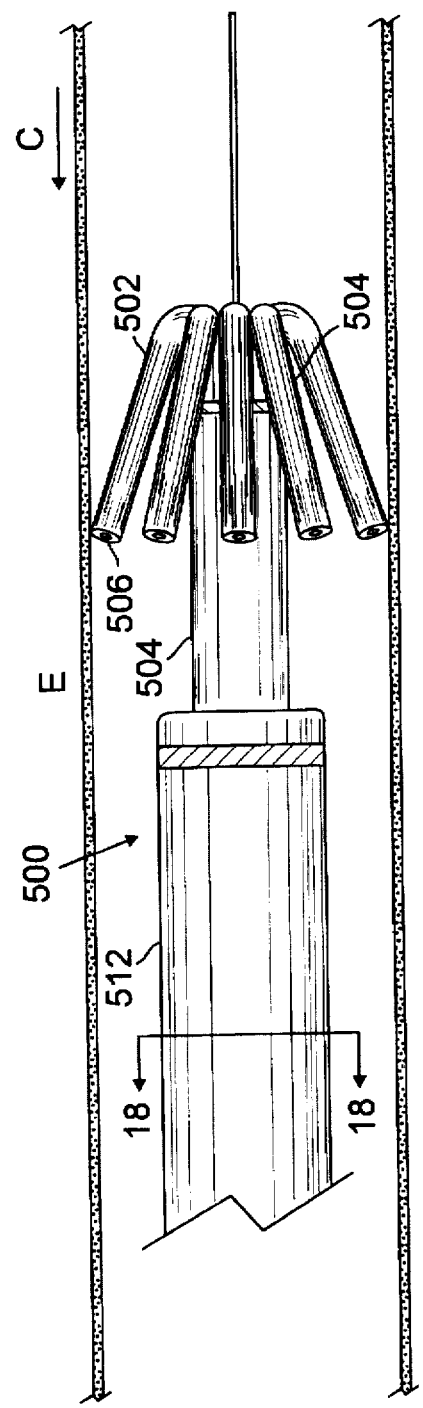
FIG. 16 is a side view of another embodiment of the present invention, deployed within a vein, for example.
Figure 17:
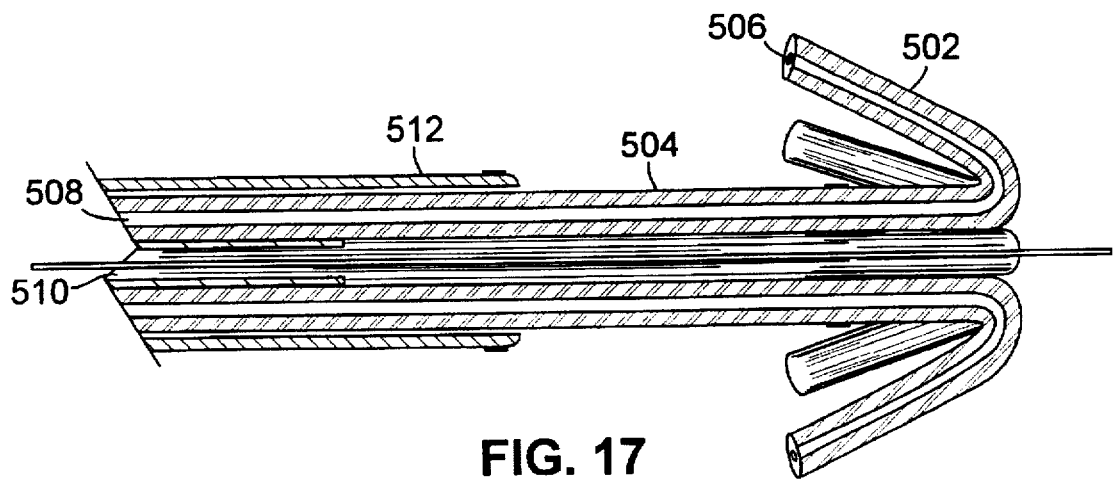
FIG. 17 is a cross-sectional view of the catheter of FIG. 16.
Figure 18:
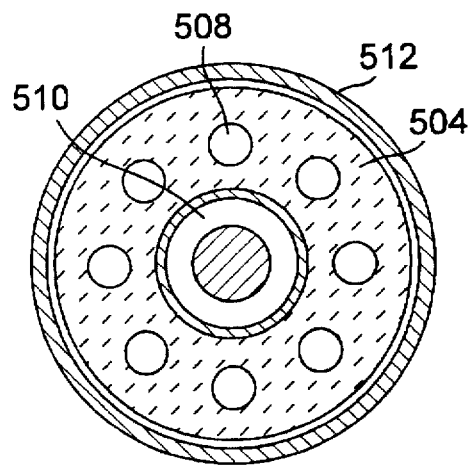
FIG. 18 is a cross-sectional view of the catheter of FIG. 16, through line 18—18.
Figure 19:
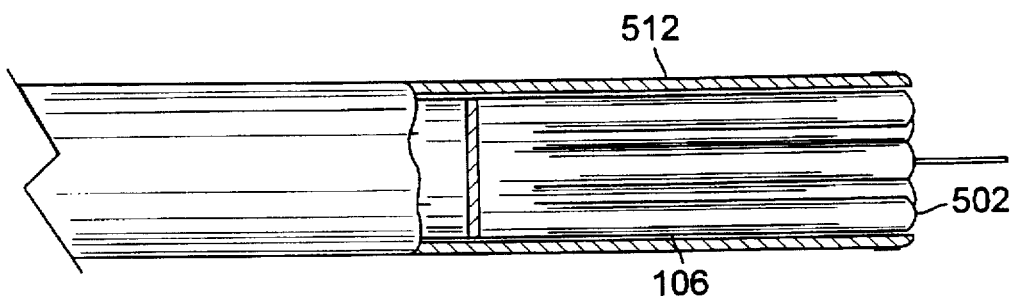
FIG. 19 is a partial cross-sectional view of the catheter of FIG. 16, with a portion of the sleeve in cross-section to reveal the distal portion of the shaft.
Figure 20:
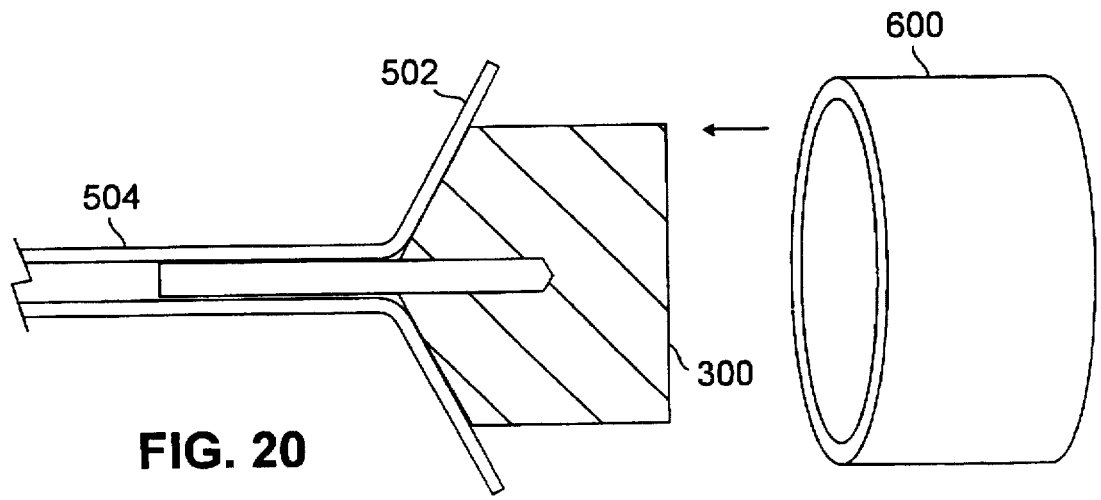

FIG. 17 is a cross-sectional view of the catheter 500 of FIG. 16, showing the delivery lumens 508 and guide wire lumen 510. FIG. 18 is a cross-sectional view of the catheter 500 through line 18—18 in FIG. 16. FIG. 19 is a cross-sectional view of the catheter 500 wherein the delivery members 502 are received within and compressed by the sleeve 512. The proximal portion of the catheter 500 can be the same as that shown in FIG. 5.

As above, the dimensions of the catheter 500 depend on the intended site. For example, the cerebral arteries have a diameter of about 1.0–2.5 mm. Veins, on the other hand, can have diameters of about 6-10 mm. The members 502 preferably have a diameter when fully flared slightly greater than the diameter of the vessel itself, to ensure that they bear against the walls of the vessel. The delivery members 502 preferably rotate through an angle between 115°-140° to reach the position of FIG. 16.

To treat thrombosis, for example, with this embodiment of the invention, the catheter 500 can be inserted through a guide catheter and over a guide wire, through the thrombus. When the distal portion of the catheter is positioned sufficiently beyond the distal portion of the thrombus, the sleeve 512 can be retracted, releasing the delivery members 502 which rotate through an obtuse angle to the position of FIG. 18. The catheter 500 may need to be advanced slightly to enable the delivery members 502, whose diameter is slightly larger than that of the vessel, to fully rotate. A lytic agent, such as urokinase, streptokinase or rTPA, is then delivered. Integralin may be delivered, as well. Any other drug or agent known or to be developed which is efficacious in dissolving a thrombus, may also be used. Blood flow and the pressure of delivery carry the delivered drug towards the thrombus. The drug is administered until the thrombus is dissolved. When the thrombus is dissolved, the sleeve can be advanced over the distal portion of the catheter prior to its withdrawal.

This configuration can also be used as a filter to catch and remove a thrombus or plaque. The members 502 can be solid, or can include lumens and a series of ports along its surfaces for drug delivery, to dissolve material caught by the members 502. The catheter 500 can be inserted through and beyond a thrombus, and deployed. The distal portion of the catheter can then be withdrawn into the guide catheter, which would be positioned proximal to the thrombus, together with the thrombus.

Alternatively, the catheter can be deployed in a location within a vein or artery to catch thrombolytic material which may pass. A lytic agent, such as those discussed above, can be delivered prior to and during removal of the thrombolytic material by the members. A plurality of ports to allow the delivery of drug along the inside surface of the delivery member can be provided to enable the delivery of a lytic agent directly onto thrombolytic material caught by the members 502. This embodiment could be particularly useful in cerebral arteries.

It may also be advantageous to use the embodiment of FIGS. 1–4 and 16–19 together to apply lytic agent to the proximal and distal sides of the thrombus. First, the catheter 100 can be deployed proximal to the thrombus. Then the catheter 500 can be advanced through and distal to the thrombus over the same guide wire 114 as the catheter 100, through the guide wire lumen 116 of the catheter 100. Alternatively, the catheter 500 could be deployed first distal to the thrombus and the embodiment of catheter 100 can then be advanced over it. Lytic agent can then be simultaneously or sequentially supplied through both catheters.

Figure 21:
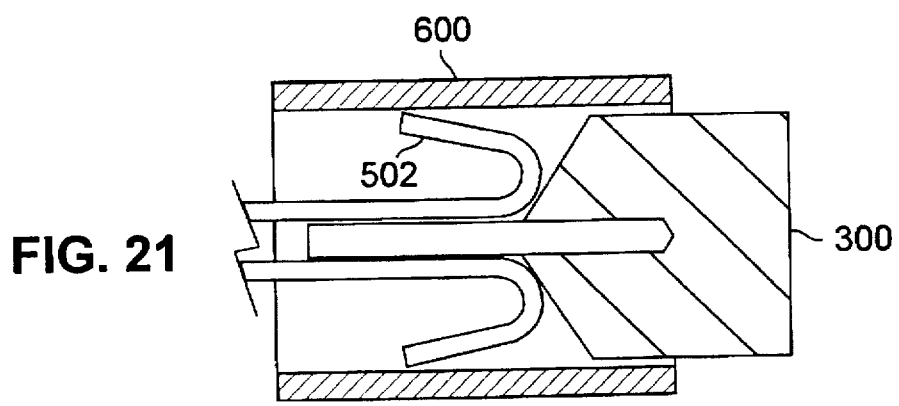
Figure 22A:
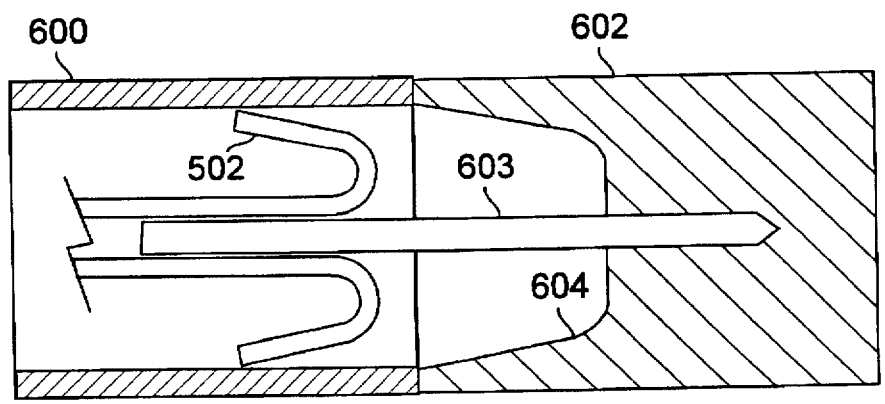

FIGS. 20–23 illustrate the formation of the embodiment of FIGS. 16–19. After cutting the distal portion of the shaft 504, the tool 300 of FIG. 12 is used to flare the members 502. When the members extend past the side walls of the tool 300, as in FIG. 20, a tube or collar 600 is advanced over the distal end of the tool, engaging and forcing the portions of the delivery members backward, as shown in FIG. 21. The first tool is then removed and a second tool 602, shown in cross-section in FIG. 22, is attached to the collar 600. A wire or mandrel 603 depends from the tool 602 and is inserted into the shaft as shown. The second tool 602 is configured to match the desired position of the members 502 when fully deployed. The shaft is advanced in the direction of the arrow from the collar 600 into the second tool 602, over the wire 603. When the shaft 104 is completely within the second tool 602, the delivery members 502 conform to the curvature of the surfaces 604 of the second tool 602, as shown in FIG. 23. The collar 600 is then removed.

The catheter shaft with the tool 602 in place is heated at about 225°–250° F. for 5–30 minutes. The catheter shaft is then prepared as above.

Figure 25:
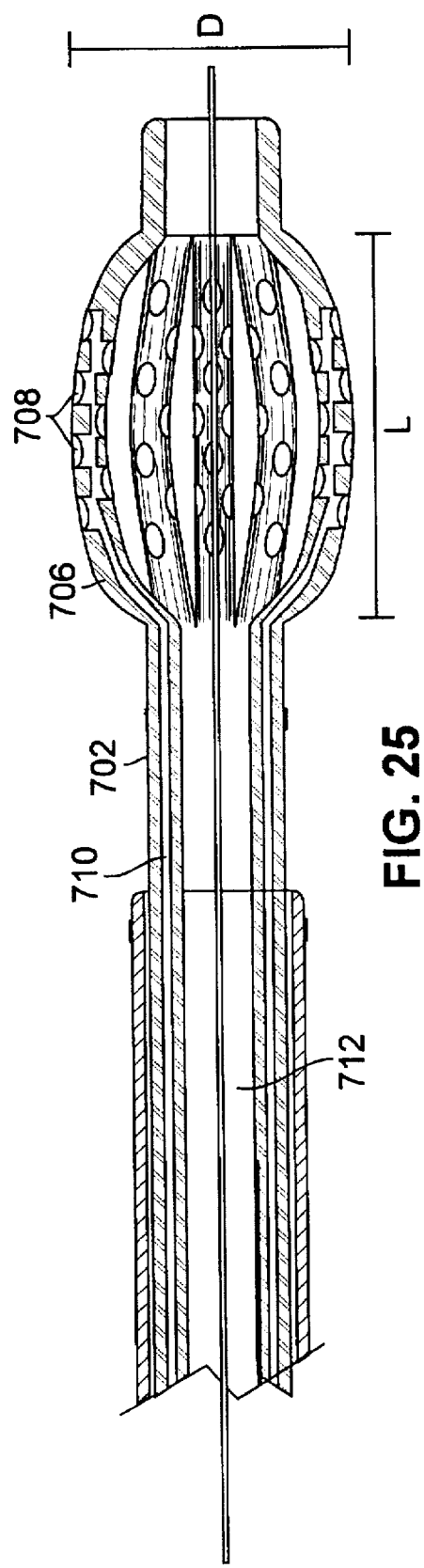
FIG. 25 is a cross-sectional view of the catheter of FIG. 24.
Figure 26:
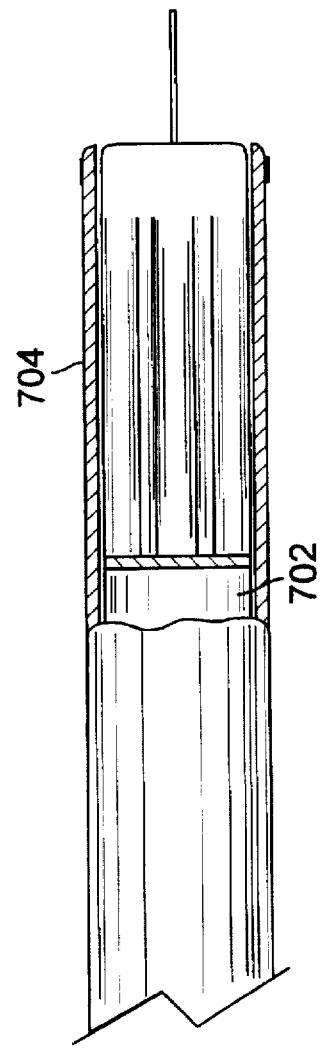
FIG. 26 is a partial cross-sectional view of the catheter of FIG. 24 in its compressed position, wherein the sleeve is partially cut away to reveal the distal portion of the shaft.

FIGS. 24–26 illustrate a catheter 700 with an expandable distal portion which can be used for drug delivery, as a thrombolytic filter with clot lysing capability, or merely as a thrombolytic filter, in accordance with another embodiment of the invention. FIG. 24 is a side view of the catheter 700 in its deployed position in the vena cava, for example. The catheter 700 comprises a shaft 702 with an expandable distal portion and a means for compressing the expandable portion, preferably a sleeve 704. Other means for compressing, as described above, may be used as well. The distal portion preferably comprises a plurality of longitudinal ribs 706 having proximal and distal ends depending from the shaft 702. Other configurations, such as overlapping ribs, can also be used. A central portion of the ribs 706 flare radially beyond the outer diameter of the catheter shaft, between the proximal and distal ends of the ribs 706. A portion of the ribs 706 preferably bear against the wall of the vena cava, as shown in FIG. 24. As above, the diameter D of the ribs 706 in their fully flared position, measured across the center of the outer periphery of a region defined by the ribs, as shown in FIG. 25, is preferably greater than the diameter of the site, ensuring that the ribs bear against the wall, as shown in FIG. 24.

The longitudinal ribs 706 can be of any desired length, and preferably vary between 6–10 mm. The greatest diameter D of the longitudinal ribs 706 when fully flared is preferably 1.5–2 times their length L, as shown in FIG. 25. Eight lumens are provided in this embodiment, but more or less can be used, depending on the size of the lumen or vessel at the site of interest.

At least one and preferably a series of ports 708 are provided in each rib 706. Delivery lumens 710 provide drugs or other agents to the ports 708, as shown in FIG. 25. A guide wire lumen 712 is provided, as well. If only to be used for drug delivery to the walls of the vessel, such as to prevent restenosis, the ports 708 preferably extend outward. If the catheter is to be used as a thrombolytic filter, additional ports are preferably provided at the sides of the ribs, for drug delivery between the ribs, and along the underside of the ribs, for drug delivery to the region within the ribs. The ports 708 are preferably about 0.005 inches, and can be formed by a punch, drill or laser. Slits, which can be made by a blade or laser, can be used for drug delivery, as well. A lytic agent, such as those discussed above, or any other useful drug or agent known or to be discovered, can be delivered to dissolve thrombolytic material caught by the filter. The proximal portion of the catheter 700 can be the same as that shown in FIG. 5. The remainder of catheter 700 can be the same as the embodiments above.

FIG. 26 is a partial sectional view of the catheter of FIG. 24, wherein the distal portion of the shaft is completely within the sleeve 704. The sleeve compresses the distal portion of the shaft so that its diameter is less than that of the sleeve 704. The catheter 700 is stored, advanced to the desired site, and preferably withdrawn in this configuration.

The catheter 700 can be advanced to its desired site through a guide catheter, for example, in the configuration of FIG. 26. When the site is reached, the sleeve 704 is retracted, releasing the distal portion of the catheter shaft, allowing the longitudinal ribs 706 to flare outward as shown in FIG. 24. Blood or other fluids can flow through the region defined by the ribs 706. Thrombolytic material greater than the distance between the ribs will be caught by the ribs. When the filter is to be removed, the sleeve 704 is advanced or the shaft 702 is retracted such that the distal portion of the shaft is within the sleeve.

If only filtration is desired, the ribs can be solid. No delivery lumens would then be required, either.

Figure 27:
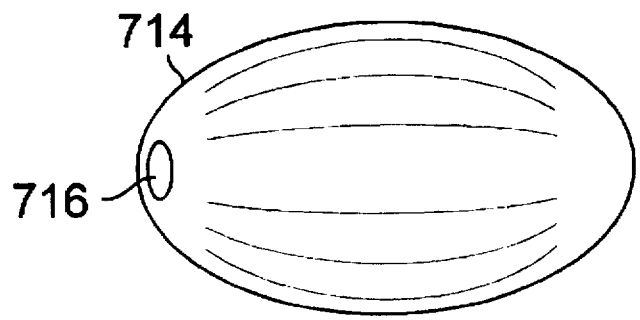
FIG. 27 is a side view of a tool used in the manufacture of the catheter of FIG. 25.
Figure 28:
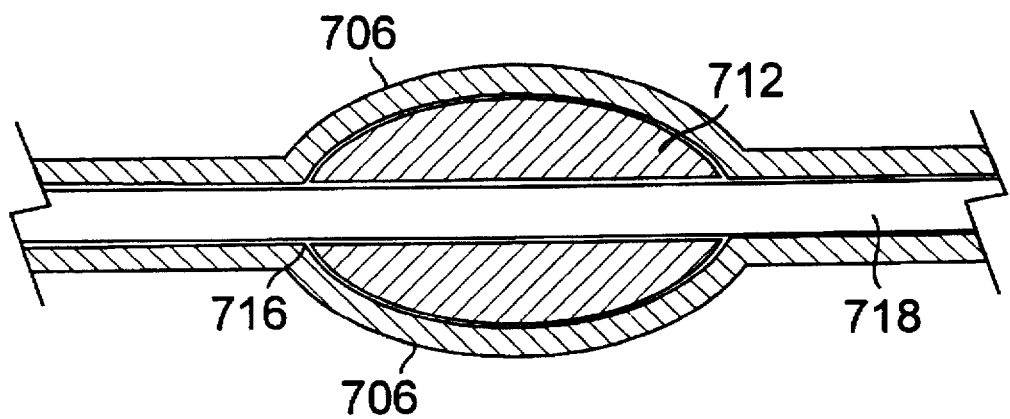
FIG. 28 is a cross-sectional view of the tool of FIG. 27, in position during the manufacture of the catheter of FIG. 25.

The catheter 700 of this embodiment can be manufactured of the same materials as described above. The catheter shaft 702 is first extruded, including the delivery lumens 710 if necessary. A wire is then inserted through the distal portion of the guide wire lumen 712. A series of radial longitudinal cuts which do not extend to the distal end of the shaft, are then made with a cutting blade or razor through the shaft, to the guide wire lumen 712, to define the longitudinal ribs 706. The wire is removed and an oblong shaped tool 714, made of brass, stainless steel or PTFE, for example, is then inserted between the ribs. A perspective view of the tool 714 is shown in FIG. 27. A cross-sectional view of the tool 712 and two ribs 706 is shown in FIG. 28. The tool preferably includes an opening 716 along its longitudinal axis for receiving a wire 718 inserted through the distal end of the shaft 702. The wire 718 helps to maintain the tool 714 centered between the ribs 706. The shaft 702 and tool 714 are then heated in an oven, as above. Subsequent processing is the same as above, as well.

The above embodiments are examples of implementations of the present invention, which is defined in the following claims.

We claim:

1. A method of delivering drugs or other agents to a patient lumen comprising:

advancing a catheter having compressed delivery members through and beyond a thrombus prior to a releasing step;

releasing the delivery members so that the thrombus will be caught between the delivery members and a shaft of the catheter;

delivering drugs or other agents through the catheter and delivery members.

2. The method of claim 1, further comprising removing the thrombus using the delivery members, by retracting the catheter.

3. A method of treating thrombosis comprising:

advancing a first catheter with compressed delivery members proximal to the thrombus;

advancing a second catheter with compressed delivery members through and beyond the thrombus;

releasing the delivery members of the first catheter;

releasing the delivery members of the second catheter so that the thrombus will be caught between the delivery members of the first catheter and the delivery members of the second catheter;

delivering drugs or other agents through the second catheter.

4. The method of claim 3, further comprising removing the thrombus by retracting the second catheter.

5. The method of claim 3, wherein the delivery steps comprise delivering a lytic agent through the first and second catheters.

6. A method comprising:

advancing a distal portion of a catheter having compressed, expandable solid members through a thrombus;

releasing the members to extend rearwardly from a distal end of the catheter so that the thrombus will be caught between the members and a shaft of the catheter; and removing the thrombus by retracting the catheter.

7. The method of claim 6, wherein the thrombus is removed by retracting the catheter into a guide catheter.

* * * * *

UNITED STATES PATENT AND TRADEMARK OFFICE
CERTIFICATE OF CORRECTION

PATENT NO. : 5,713,853
DATED : FEBRUARY 3, 1998
INVENTOR(S) : CLARK ET AL.

It is certified that error appears in the above-identified patent and that said Letters Patent is hereby corrected as shown below:

[57] Abstract: delete entire abstract paragraph and insert ---Methods for treating thrombosis are disclosed using a catheter with a self-expanding portion. The catheter is advanced with compressed members proximal to the thrombus, the expandable members are released, and the thrombus may be removed by retracting the catheter or drugs may be delivered to the thrombus through the expandable members.---

Col. 1, lines 4-8 (Field of the Invention): delete the entire paragraph and insert ---Method for treating thrombosis with a self-expanding portion of a drug delivery catheter.---

Col. 2, lines 54-67: delete all text in this line number range.

Col. 3, lines 1-55: delete all text in this line number range.

Col. 11, line 46: "250°" should read ---25°---

Signed and Sealed this

Fourteenth Day of September, 1999

*Attest:*

Q. TODD DICKINSON

*Attesting Officer*   *Acting Commissioner of Patents and Trademarks*